US012324795B2

(12) United States Patent
Suzuki et al.

(10) Patent No.: US 12,324,795 B2
(45) Date of Patent: Jun. 10, 2025

(54) AUTOPHAGY ACTIVATING AGENT

(71) Applicant: WAKUNAGA PHARMACEUTICAL CO., LTD., Osaka (JP)

(72) Inventors: Junichiro Suzuki, Akitakata (JP); Yukihiro Kodera, Akitakata (JP); Satomi Miki, Akitakata (JP)

(73) Assignee: WAKUNAGA PHARMACEUTICAL CO., LTD., Osaka (JP)

( * ) Notice: Subject to any disclaimer, the term of this patent is extended or adjusted under 35 U.S.C. 154(b) by 909 days.

(21) Appl. No.: 16/972,414

(22) PCT Filed: Jun. 6, 2019

(86) PCT No.: PCT/JP2019/022637
§ 371 (c)(1),
(2) Date: Dec. 4, 2020

(87) PCT Pub. No.: WO2019/235597
PCT Pub. Date: Dec. 12, 2019

(65) Prior Publication Data
US 2021/0228521 A1    Jul. 29, 2021

(30) Foreign Application Priority Data

Jun. 7, 2018   (JP) .................................. 2018-109700

(51) Int. Cl.
| | | |
|---|---|---|
| *A61K 31/198* | (2006.01) | |
| *A23L 33/175* | (2016.01) | |
| *A61K 9/00* | (2006.01) | |
| *A61K 36/8962* | (2006.01) | |

(52) U.S. Cl.
CPC .......... *A61K 31/198* (2013.01); *A23L 33/175* (2016.08); *A61K 9/0053* (2013.01); *A61K 36/8962* (2013.01); *A61K 2236/333* (2013.01); *A61K 2236/53* (2013.01)

(58) Field of Classification Search
None
See application file for complete search history.

(56) References Cited

U.S. PATENT DOCUMENTS

| | | | |
|---|---|---|---|
| 6,239,111 | B1 | 5/2001 | Moriguchi et al. |
| 7,201,929 | B1 | 4/2007 | Finkelstein |
| 2017/0360731 | A1 | 12/2017 | Suzuki et al. |
| 2018/0147170 | A1 | 5/2018 | Ushijima et al. |

FOREIGN PATENT DOCUMENTS

| | | |
|---|---|---|
| JP | 9-315965 A | 12/1997 |
| JP | 2010-106001 A | 5/2010 |
| JP | 2014-23449 A | 2/2014 |
| KR | 10-2015-0090646 | 8/2015 |
| WO | WO 2016/088892 A1 | 6/2016 |
| WO | WO 2016/199885 A1 | 12/2016 |

OTHER PUBLICATIONS

"Thinking About Your Risk for Alzheimer's Disease? Five Questions To Consider" (https://www.nia.nih.gov/health/alzheimers-causes-and-risk-factors/thinking-about-your-risk-alzheimers-disease-five (accessed Nov. 2023)).*
Javed (Brain Research (2011), vol. 1389, pp. 133-142).*
Extended European Search Report issued Jan. 26, 2022 in European Patent Application No. 19814245.7, citing documents AO therein, 9 pages.
Khan, "Dawa-e Seer Khalli", Muheet-e-Azam, vol. II ($19^{th}$ century AD), Matba Nizami, Kanpur, 1887, p. 88 (with English translation).
Mishra, "Rasona Petaka", Ed. $2^{nd}$ 2005, p. 249 (with English translation).
Datta, "Rasona Kanda Guna", Ed. $1^{st}$ 2009, p. 93 (with English translation).
Khan, "Halwa-e-Lahsan", Qaraabaadeen, Najm-al-Ghani ($20^{th}$ Ghani century AD), Munshi Nawal Kishore, Lucknow, (Second Edition) 1928, p. 149 (with English translation).
Khan, "Zimaad-e- Piyaz Bara-e-Ghashi", Khazaain-al-Advia, vol. II ($20^{th}$ century AD), Ghani Nadeem Yunus Printer / Sheikh Mohd Basheer & Sons, Lahore, 1911, p. 117 (with English translation).
European Office Action and Third Party Observation issued on Mar. 21, 2023 in European Patent Application No. 19814245.7, citing references 21-25 therein, 4 pages.
Kevin Moreau, et al., "Cytoprotective roles for autophagy", ScienceDirect, Current Opinion in Cell Biology, 2016, pp. 206-211.
Zelda H. Cheung, et al.,"Autophagy deregulation in neurodegenerative diseases—recent advances and future perspectives", Journal of Neurochemistry (2011), pp. 317-325.
Ishrat Ahmed, et al., "Development and Characterization of a New Parkinson's Disease Model Resulting from Impaired Autophagy", The Journal of Neuroscience, Nov. 14, 2012 • 32(46): 16503-16509 • 16503.
Melinda A. Lynch-Day, et al., "The Role of Autophagy in Parkinson's Disease", Copyright # 2012 Cold Spring Harbor Laboratory Press; 13 pages.
Ziv Gan-Or, et al. "Genetic perspective on the role of the autophagylysosome pathway in Parkinson disease", Autophagy, ISSN: 1554-8627 (Print) 1554-8635, 2015.
A.R. Esteves, et al., "Acetylation as a major determinant to microtubule-dependent autophagy: Relevance to Alzheimer's and Parkinson disease pathology", Elsevier, BBA—Molecular Basis of Disease 1865 (2019) 2008-2023.
David C. Rubinsztein, et al. "Autophagy and Aging", Cell, Leading Edge Review Cell 146, Sep. 2, 2011 ͓ 2011 Elsevier Inc. 685.
Ralph A. Nixon, "Autophagy, amyloidogenesis and Alzheimer disease", Accepted Oct. 30, 2007 Journal of Cell Science 120, 4081-4091 Published by The Company of Biologists 200.

(Continued)

*Primary Examiner* — Susan Hoffman

(74) *Attorney, Agent, or Firm* — Oblon, McClelland, Maier & Neustadt, L.L.P.

(57) ABSTRACT

To provide a compound used for activating autophagy, which has few side effects and mild effects comprising S1PC or a salt thereof as an active ingredient.

16 Claims, 3 Drawing Sheets

(56) References Cited

OTHER PUBLICATIONS

Fang Guo, et al., "Autophagy in neurodegenerative diseases: pathogenesis and therapy", Brain Pathology vol. 28, Issue 1 p. 3-13, 2017.
Noboru Mizushima, "Autophagy: process and function", Genes & Development, https://genesdev_cship.org/content/21/22/2861.full, 25 pages, 2007.
International Search Report issued on Jul. 23, 2019 in PCT/JP2019/022637 filed on Jun. 6, 2019, citing documents AA-AD, AO-AS, and AAK-AAN therein, 3 pages.
Garlic Science, First Edition, 2000, pp. 93-122 (32 total pages) (with partial English translation).
Suzuki et al., "S-1-Propenylcysteine promotes the differentiation of B cells into IgA-producing cells by the induction of Erk1/2-dependent Xbp1 expression in Peyer's patches", Nutrition, 2016, vol. 32, pp. 884-889.
Matsutomo et al., "Metabolomic study on the antihypertensive effect of S-1-propenylcysteine in spontaneously hypertensive rats using liquid chromatography coupled with quadruple-Orbitrap mass spectrometry", Journal of Chromatography B, 2017, vol. 1046, pp. 147-155.
Zare-Shahabadi et al., "Autophagy in Alzheimer's Disease", Rev Neurosci., 2015, vol. 26, No. 4, pp. 1-15.
Lynch-Day et al., "The Role of Autophagy in Parkinson's Disease", Cold Spring Harbor Perspectives in Medicine, 2012, vol. 2:a009357, pp. 1-13.
Zhao et al., "Subcellular Clearance and Accumulation of Huntington Disease Protein: A Mini-Review", Frontiers in Molecular Neurocience, 2016, vol. 9, Article 27, pp. 1-4.
Ramesh et al., "Autophagy Dysregulation in ALS: When Proten Aggregates Get Out of Hand", Frontiers in Molecular Neuroscience, 2017, vol. 10, Article 263, pp. 1-18.
De Palma et al., "Skeletal muscle homeostasis in Duchenne muscular dystrophy: modulating autophagy as a promising therapeutic strategy", Frontiers in Aging Neuroscience, 2014, vol. 6, Article 188, pp. 1-8.
Sarkar et al., "Impaired autophagy in the lipid storage disorder Niemann-Pick type C1 disease", Cell Rep., NIH Public Access, 2013, vol. 5, No. 5, pp. 1-26.
Nakai et al., "The role of autophagy in cardiomyocytes in the basal state and in response to hemodynamic stress", Nature Medicine, 2007, vol. 13, No. 5, pp. 619-624.
Liang et al., "Mycobacteria and Autophagy: Many Questions and Few Answers", Curr. Issues Mol. Biol., 2017, vol. 21, pp. 63-72 (11 total pages).
Netea-Maier et al., "Modulation of inflammation by autophagy: Consequences for human disease", Autophagy, 2016, vol. 12, No. 2, pp. 245-260.
Evans et al., "Target Acquired: Selective Autophagy in Cardiometabolic Disease", Sci Signal., 2017, vol. 10, No. 468, pp. 1-38.
Kodera et al., "Chemical and Biological Properties of S-1-Propenyl-L-Cysteine in Aged Garlic Extract", Molecules, 2017, vol. 22, Article 570, pp. 1-18.
Carson et al., "The Synthesis and Base-Catalyzed Cyclization of (+)- and (−)-cis-S-(I-propenyl)-L-cysteine Sulfoxides", The Journal of Organic Chemistry, 1966, vol. 31, No. 9, pp. 2862-2864.
Uddin et al., "Autophagy and Alzheimer's Disease: From Molecular Mechanisms to Therapeutic Implications", Frontiers in Aging Neuroscience, 2018, vol. 10, Article 4, pp. 1-18.
Banerjee et al., "Effect of garlic on cardiovascular disorders: a review", Nutrition Journal, 2002, vol. 1, Article 4, pp. 1-14.
Chauhan, "Multiplicity of Garlic Health Effects and Alzheimer's Disease", The Journal of Nutrition, Health, & Aging, vol. 9, No. 6, 2005, pp. 421-432, XP093126154.
Calcul et al., "Natural products as a rich source of tau-targeting drugs for Alzheimer's disease", Future Med Chem., vol. 4, No. 13, Sep. 2012, pp. 1-22, XP093126085.
Chauhan, "Effect of aged garlic extract on APP processing and tau phosphorylation in Alzheimer's transgenic model Tg2576", Journal of Ethnopharmacology, vol. 108, 2006, pp. 385-394, XP025086024.
European Office Action issued on Feb. 19, 2024 in European Patent Application No. 19 814 245.7, citing documents 23-25 therein, 7 pages.
Kodera, Yukihiro, et al., "Chemistry of aged garlic: Diversity of constituents in aged garlic extract and their production mechanisms via the combination of chemical and enzymatic reactions (Review)", Experimental and Therapeutic Medicine 19: 1574-1584, 2020.
Matsutomo, Toshiaki, et al., "Development of an Analytic Method for Sulfur Compounds in Aged Garlic Extract with the Use of a Postcolumn High Performance Liquid Chromatography Method with Sulfur-Specific Detection1-3": The Journal of Nutrition Supplement—2014 International Garlic Symposium: Role of Garlic in Cardiovascular Disease Prevention, Metabolic Syndrome, and Immunology; pp. 450S-455S.
Jiménez-Amezcua, Ignacio, et al., "A Comparative Study of LC-MS and FIA-(ESI)MS for Quantitation of S-Allyl-L-Cysteine in Aged Garlic Supplements"; Foods 2024, 13, 2645. https://doi.org/10.3390/foods13172645: 13 pages.

* cited by examiner

AUTOPHAGY ACTIVATING AGENT

This application is a national stage application of PCT/JP2019/022637, filed Jun. 6, 2019, which claims priority to Japanese application 2018-109700, filed Jun. 7, 2018. The contents of both applications are incorporated herein by reference.

TECHNICAL FIELD

The present invention relates to an autophagy activating agent that enhances autophagy functions.

BACKGROUND ART

Autophagy is a system that degrades a large amount of proteins such as protein aggregates or damaged organelles, and maintains homeostasis in the living body. Protein aggregates and damaged organelles are surrounded by phagophores to form autophagosomes. Autophagosomes are bound to lysosomes to form autolysosomes, whereby degradation is initiated. Activation of autophagy is induced such that an intracellular energy sensor, AMP-activated protein kinase (AMPK), inhibits mammalian target of rapamycin (mTOR) which negatively regulates autophagy, and thus unc-51 like kinase (ULK) complex is activated. The ULK complex activates various autophagy related genes (Atg). In particular, Atg7 is an important protein in the process of binding phosphatidylethanolamine to microtubule-associated protein light chain 3 (LC3) and changing it to LC3-II by ubiquitin-like enzyme activity. LC3-II induces autophagy by elongating and closing the phagophore.

Although autophagy non-selectively degrades intracellular proteins, there is a mechanism that selectively degrades, for example, protein aggregates. Protein aggregates are ubiquitinated and recognized by the ubiquitin-binding protein p62. P62 bound to ubiquitinated protein aggregates is bound to LC3, whereby the resultant aggregates are selectively degraded by autophagy.

A decrease in autophagy function is thought to cause various diseases such as neurodegenerative disease, cardiovascular disease, lung disease, and infectious disease. In recent years, a relationship between autophagy and diseases such as Alzheimer's disease, Parkinson's disease, Huntington's disease, amyotrophic lateral sclerosis (ALS), muscular dystrophy, Niemann-Pick disease, heart failure, dilated cardiomyopathy, infectious disease, chronic inflammation, and fatty liver have been reported, which suggests that the decrease in autophagy function is involved in the onset of each of the diseases. Therefore, the activation of autophagy is considered to be useful for prevention or treatment of these diseases.

For example, Non Patent Literature 4 discloses that, in Alzheimer's disease, autophagy function is decreased in the early phase, and tau protein aggregates to be normally degraded by autophagy are accumulated in cells, which leads to the Alzheimer's onset.

Non Patent Literature 5 discloses that the cause of Parkinson's disease is the accumulation of α-synuclein protein due to a decrease in autophagy function, which is likely to be improved by the activation of autophagy.

Non Patent Literature 6 discloses that Huntington's disease is triggered by the accumulation of mutant huntingtin (mutant Htt), and mutant Htt is degraded by a ubiquitin-proteasome system and autophagy.

Non Patent Literature 7 discloses that ALS is caused by dysfunction of motor neurons caused by incorrect localization of disease-related proteins and formation of protein aggregates, and a decrease in autophagy function causes neurodegeneration, including ALS.

Non Patent Literature 8 discloses that the activation of autophagy is maintained at a certain level in muscle; however, when the level of activation is increased, muscle wasting is promoted, and the level is reduced to cause the accumulation of abnormal proteins and organelles, and that a decrease in autophagy function is known in muscular dystrophy, and the activation of autophagy leads to its treatment.

Non Patent Literature 9 indicates that Niemann-Pick disease is caused by intracellular cholesterol accumulation based on non-formation of amphisomes which are formed by the fusion of autophagosomes and endosomes; a decrease in autophagy function and cholesterol accumulation occur in Npc knockout mice or mutant mice, and the same pathological condition as Niemann-Pick disease is shown; and the same pathological condition as Niemann-Pick disease is suppressed by adding rapamycin as an inducer of autophagy to Npc mutant mice or cell lines, and suggest that an effective treatment can be achieved by inducing autophagy.

Non Patent Literature 10 discloses that autophagy changes are associated with heart diseases such as cardiac hypertrophy and heart failure, dilation and systolic dysfunction of left ventricle occur in t mice deficient in Atg5, which is a protein inducing the activation of autophagy, thereby inducing cardiac hypertrophy.

Non Patent Literature 11 discloses that *Mycobacterium tuberculosis* which is the cause of tuberculosis is escaped to the cytoplasm by inhibiting the formation of phagosomes in host cells such as macrophages, and the amount of *Mycobacterium tuberculosis* in the host cells is controlled by autophagy.

Non Patent Literature 12 discloses that the balance between biological defense and inflammation is maintained by autophagy, and a decrease in autophagy function causes cancer, autoimmune diseases, and neurodegenerative diseases.

Non Patent Literature 13 discloses that a decrease in function of lipophagy involved in degradation of lipids is associated with fatty diseases such as obesity, diabetes, arteriosclerosis, and steatohepatitis, and the activation of autophagy is likely to be the target of treatment.

Garlic has been used not only as a food but also for the treatment of various diseases since ancient times. A characteristic component of garlic is γ-glutamyl-S-1-propenylcysteine. When garlic is cut, crushed, grated or aged, the component is converted into water-soluble S-1-propenylcysteine (hereinafter abbreviated as "S1PC") by an enzyme called as γ-glutamyl transpeptidase contained in garlic. Examples of such a water-soluble compound which is generated by the above enzymatic reaction include S-methyl cysteine, S-allyl cysteine (hereinafter abbreviated as "SAC"), for example, in addition to S1PC (Non Patent Literature 1).

S1PC has been reported to have an immunomodulatory effect (Non Patent Literature 2 and Patent Literature 1) and an antihypertensive effect (Non Patent Literature 3 and Patent Literature 2); however, it has not been completely known about activation of autophagy.

CITATION LIST

Patent Literature

Patent Literature 1: WO 2016/088892 A
Patent Literature 2: WO 2016/199885 A

Non Patent Literature

Non Patent Literature 1: Garlic Science, First Edition, 93-122, 2000
Non Patent Literature 2: Nutrition., 2016, 32, 884-9
Non Patent Literature 3: J Chromatogr B Analyt Technol Biomed Life Sci., 2017 1046, 147-155.
Non Patent Literature 4: Rev Neurosci. 2015; 26 (4): 385-395.
Non Patent Literature 5: Cold Spring Harb Perspect Med. 2012 2 (4), a009357.
Non Patent Literature 6: Front Mol Neurosci. 2016; 9:27.
Non Patent Literature 7: Front Mol Neurosci. 2017; 10:263
Non Patent Literature 8: Front Aging Neurosci. 2014; 6:188
Non Patent Literature 9: Cell Rep. 2013; 5 (5): 1302-15.
Non Patent Literature 10: Nat Med. 2007; 13 (5): 619-24.
Non Patent Literature 11: Curr Issues Mol Biol. 2017; 21:63-72.
Non Patent Literature 12: Autophagy. 2016; 12 (2): 245-6
Non Patent Literature 13: Sci Signal. 2017; 10 (468)

SUMMARY OF INVENTION

Technical Problem

The present invention relates to provision of a compound used for activating autophagy, which has few side effects and mild effects.

Solution to Problem

The inventors of the present invention have conducted various studies on the usefulness of S1PC or a salt thereof. As a result, they have found that S1PC or a salt thereof has an excellent autophagy activating effect, and further has an apoptosis inhibitory effect and a tau protein-removing effect, and is useful as an autophagy activating agent and an agent for preventing, treating, or ameliorating a neurodegenerative disease, thus completing the present invention.

That is, the present invention relates to the following 1) to 10):

1) An autophagy activating agent comprising S1PC or a salt thereof as an active ingredient;
2) The autophagy activating agent according to 1), wherein when the total of a trans-isomer and a cis-isomer is 100%, the proportion of the trans-isomer in S1PC is from 50 to 100%.
3) The autophagy activating agent according to 1) or 2), wherein the S1PC or a salt thereof is derived from at least one *Allium* plant selected from the group consisting of garlic, onion, elephant garlic, Chinese chive, and spring onion;
4) The autophagy activating agent according to 3), wherein the S1PC or a salt thereof is obtained by extracting the *Allium* plant in a 10 to 50% ethanol solution at 0 to 80° C. for 1 month or more, allowing the obtained extract to adhere to a cation exchange resin, eluting the adsorbate with 0.1 to 3 N ammonia water, subjecting the eluate to silica gel column chromatography and/or reverse phase column chromatography, and collecting the resulting eluate;
5) The autophagy activating agent according to any one of 1) to 4), wherein the agent is a medicine;
6) The autophagy activating agent according to any one of 1) to 4), wherein the agent is a food;
7) The autophagy activating agent according to any one of 1) to 6) for use in prevention, treatment, or amelioration of Alzheimer's disease, Parkinson's disease, Huntington's disease, amyotrophic lateral sclerosis, muscular dystrophy, heart failure, dilated cardiomyopathy, infectious disease, autoimmune disease, obesity, diabetes, arteriosclerosis, or steatohepatitis;
8) A food for activating autophagy comprising S1PC or a salt thereof as an active ingredient;
9) An agent for preventing, treating, or ameliorating a neurodegenerative disease comprising S1PC or a salt thereof as an active ingredient;
10) A food for preventing or ameliorating a neurodegenerative disease comprising S1PC or a salt thereof as an active ingredient;
11) Use of S-1-propenylcysteine or a salt thereof for producing an autophagy activating agent.
12) S-1-propenylcysteine or a salt thereof for use in activation of autophagy;
13) A method for activating autophagy comprising administering S-1-propenylcysteine or a salt thereof to a subject;
14) Use of S-1-propenylcysteine or a salt thereof, which is used for producing an agent for preventing, treating, or ameliorating a neurodegenerative disease, or a food for preventing or ameliorating a neurodegenerative disease;
15) S-1-propenylcysteine or a salt thereof, for use in prevention, treatment, or amelioration of a neurodegenerative disease; and
16) A method for preventing, treating, or ameliorating a neurodegenerative disease comprising administering S-1-propenylcysteine or a salt thereof to a subject.

Advantageous Effects of Invention

S1PC or a salt thereof, which is an active ingredient for activating autophagy in the present invention, has an excellent autophagy effect, and further has an apoptosis inhibitory effect and a tau protein-removing effect. The component is a plant-derived compound that has been eaten by humans for many years. Therefore, according to the present invention, it is possible to, with high safety, prevent, treat, or ameliorate diseases caused by a decrease in autophagy function, such as neurodegenerative diseases.

DESCRIPTION OF EMBODIMENTS

Figure 1:
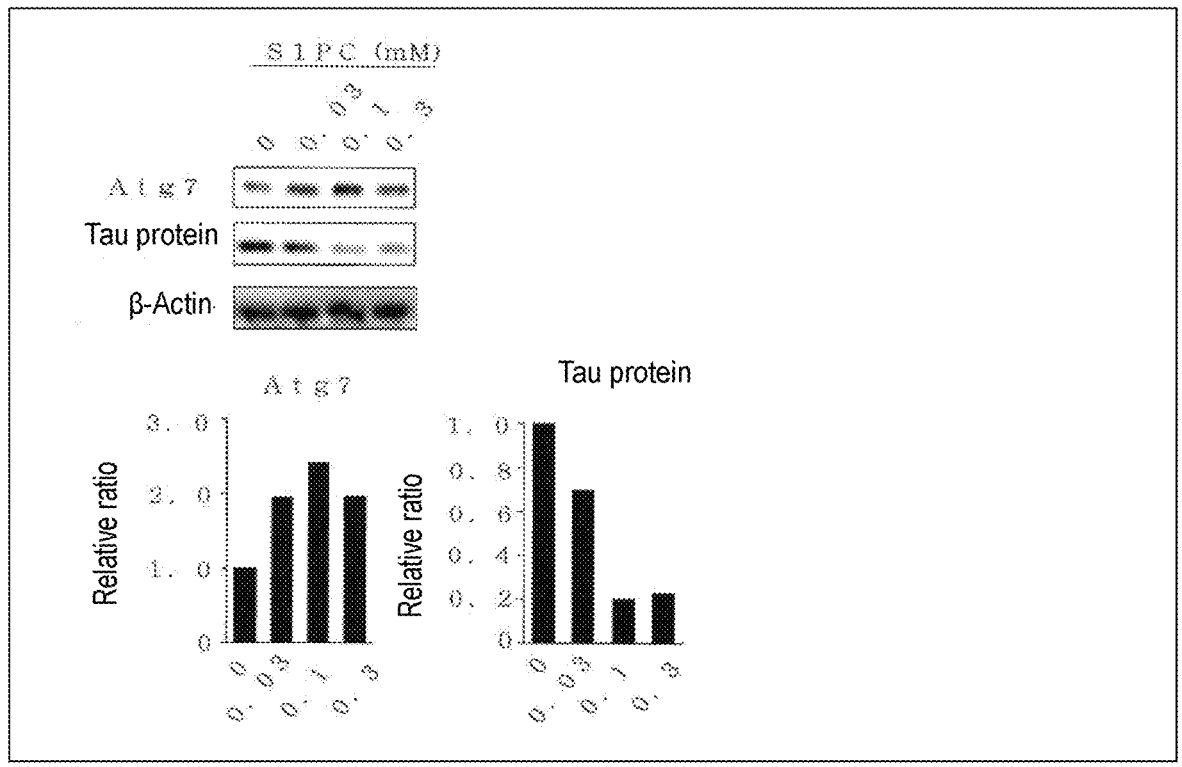
FIG. 1 illustrates an autophagy activating effect and a tau protein removing effect of S1PC.

In the present invention, S1PC is a cysteine derivative represented by the following Formula (1).

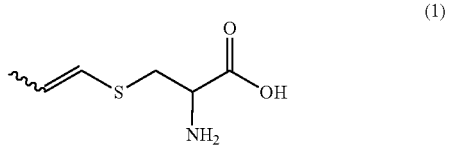
(1)

This compound has a cis or trans configuration as indicated by a wavy line in Formula (1), and the proportion of the trans-isomer is preferably high. When the total of the trans-isomer and the cis-isomer is 100%, the proportion of the trans-isomer is more preferably from 50 to 100%, still more preferably from 75 to 100%, still more preferably from 80 to 100%, and still more preferably from 90 to 100%.

Further, since the compound has an asymmetric carbon derived from cysteine, an optical isomer is present therein and it may be in any of D-form, L-form, and racemic form.

The salt of S1PC may be either an acid addition salt or a base addition salt. Examples of the acid addition salt include (a) salts with mineral acids such as hydrochloric acid, sulfuric acid, nitric acid, and phosphoric acid; (b) salts with organic carboxylic acids such as formic acid, acetic acid, citric acid, fumaric acid, gluconic acid, malic acid, succinic acid, tartaric acid, trichloroacetic acid, and trifluoroacetic acid; and (c) salts with sulfonic acids such as methanesulfonic acid, benzenesulfonic acid, p-toluenesulfonic acid, mesitylenesulfonic acid, and naphthalenesulfonic acid. Further, examples of the base addition salt include (a) salts with alkali metals such as sodium and potassium; (b) salts with alkaline earth metals such as calcium and magnesium; (c) ammonium salts; and (d) salts with nitrogen-containing organic bases such as trimethylamine, triethylamine, tributylamine, pyridine, N,N-dimethylaniline, N-methyl piperidine, N-methyl morpholine, diethylamine, dicyclohexylamine, procaine, dibenzylamine, N-benzyl-β-phenethylamine, 1-ephenamine, and N,N'-dibenzyl ethylenediamine.

Further, S1PC or a salt thereof can exist not only in an unsolvated form but also in the form of a hydrate or solvate. The hydrate or solvate may exist as any crystal form depending on manufacturing conditions. Therefore, S1PC or a salt thereof in the present invention includes all stereoisomers, hydrates, and solvates, and includes all polymorphic crystal forms or amorphous forms.

S1PC or a salt thereof in the present invention can be obtained by an organic synthesis method [1] H Nishimura, A Mizuguchi, J Mizutani, Stereoselective synthesis of S-(trans-prop-1-enyl)-cysteine sulphoxide. Tetrahedron Letter, 1975, 37, 3201-3202; 2] J C Namyslo, C Stanitzek, A palladium-catalyzed synthesis of isoalliin, the main cysteine sulfoxide in Onion (*Allium cepa*). Synthesis, 2006, 20, 3367-3369; 3] S Lee, J N Kim, D H Choung, H K Lee, Facile synthesis of trans-S-1-propenyl-L-cysteine sulfoxide (isoalliin) in onions (*Allium cepa*). Bull. Korean Chem. Soc. 2011, 32 (1), 319-320], a biochemical method using enzymes or microorganisms or a method of combination thereof. In addition to these methods, S1PC or a salt thereof can be obtained by extracting and purifying it from a plant containing the compound, e.g., an *Allium* plant or a processed product thereof.

Therefore, S1PC or a salt thereof of the present invention to be used may be not only an isolated and purified product, but also a crude product and a fraction in which the amount of S1PC or a salt thereof contained has been increased by extraction operation from the plant.

Here, examples of the *Allium* plant containing S1PC or a salt thereof include garlic (*Allium sativum* L.), onion (*Allium cepa* L.), elephant garlic (*Allium apeloprazum* L.), Chinese chive (*Allium tuberosum*. Rottl. Ex K. Spreng.), and spring onion (*Allium fistulosum* L.). These plants may be used singly, or in combination thereof. Further, the *Allium* plants may be used as they are or may be used after removing their outer skins if necessary and cutting or shredding them. Alternatively, products obtained by powdering these plants, or products obtained by extracting these plants with a solvent capable of producing a medicine or food may be used. Examples of the solvent include water and alcohol, and those obtained by adding an acid or a basic substance to the solvent.

When an extraction fraction from the *Allium* plant is used as S1PC or a salt thereof in the present invention, the fraction can be obtained, for example, by 1) extracting the *Allium* plant in a 10 to 50% ethanol aqueous solution at 0 to 80° C. for 1 month or more; and 2) subjecting the obtained extract to solid liquid separation and collecting ethanol-eluted fractions.

The ethanol aqueous solution used in the step 1) may be a 10 to 50% ethanol aqueous solution, and is preferably an ethanol aqueous solution prepared to have an ethanol concentration of 20 to 40%. Further, the treatment temperature may be set to a range of 0 to 80° C., and is preferably from 10 to 60° C. and more preferably from 20 to 40° C. The duration of the extraction treatment under the above conditions is at least one month, preferably from 1 to 20 months and more preferably from 1 to 10 months. Taking into consideration, for example, sanitation and volatility of ethanol, the present step may be performed in an airtight state, in a hermetically sealed state or in a closed container. It is preferred to use the closed container.

In the step 2), the extract obtained in the step 1) is subjected to solid liquid separation, and then ethanol-eluted fractions are collected. The collected product is concentrated as appropriate so that an extraction fraction containing S1PC or a salt thereof can be obtained. The extraction fraction may be directly used and may be used after being appropriately dried by spray drying, for example.

Further, S1PC or a salt thereof can be isolated from the extraction fraction containing S1PC or a salt thereof by combining a dialysis method using a dialysis membrane with a molecular exclusion size of 3000 to 4000, if necessary, an adhesion/separation method using a cation exchange resin, and a separation/purification method based on normal phase chromatography or reverse phase chromatography.

Here, examples of the adhesion/separation method using a cation exchange resin include a method of allowing the obtained extract to adhere to a cation exchange resin (e.g., Amberlite (Dow Chemical Company), DOWEX (manufactured by Dow Chemical Company), DIAION (manufactured by Mitsubishi Chemical Corporation)) and eluting with 0.1 to 3 N ammonia water.

Examples of the normal phase chromatography include a method of eluting with a mixture of chloroform/methanol/water using a silica gel column.

Examples of the reverse phase chromatography include a method of eluting with a 0.01 to 3% formic acid aqueous solution using an octadecyl silyl column.

Preferably, there is a method including the steps of: dialyzing the above ethanol-extracted fraction (dialysis membrane; molecular exclusion size: 3000 to 4000); allowing the dialysate to adsorb to a cation exchange resin; eluting the adsorbate with 0.5 to 2 N ammonia water; subjecting the eluate to silica gel column chromatography (solvent: a mixture of chloroform/methanol/water) to collect fractions containing a target substance; and further subjecting the collected fractions to reverse phase column chromatography for fractionation (solvent: a 0.1 to 0.5% formic acid aqueous solution) to collect a target substance.

When the total of a trans-isomer and a cis-isomer is 1008, the rate of the trans-isomer in the thus obtained S1PC is more preferably from 50 to 100%, still more preferably from 60 to 100%, and still more preferably from 70 to 100%.

Generally, S1PC or a salt thereof in the present invention has low toxicity because, for example, the $LD_{50}$ value of a dilute ethanol extract of garlic as one of the raw materials (extracted component: 14.5%, alcohol number: 1.18) is 50 ml/Kg or more in each of the oral, intra-abdominal, and subcutaneous administration routes (The Journal of Toxicological Sciences, 9, 57 (1984)), and *Allium* plants such as garlic and onion are regularly used as foods.

As shown in Examples below, S1PC or a salt thereof has an effect of increasing the amount of Atg7 protein in human neuroblasts. Atg7 is a protein involved in autophagy and is an important factor that is essential, particularly in the formation of autophagosome. As autophagy progresses, he expression level thereof increases, and it is thus regarded as an autophagy marker. Therefore, S1PC or a salt thereof has an autophagy activating effect and can serve as an autophagy activating agent.

In the present invention, "autophagy" means a system that degrades, for example, protein aggregates and damaged organelles, and activation of autophagy means promoting and enhancing the function of autophagy.

As described above, it is considered that the decrease in autophagy function is involved in many diseases such as neurodegenerative disease, cardiovascular disease, lung disease, and infectious disease (Non Patent Literatures 4 to 13). Therefore, the autophagy activating agent of the present invention is useful as an agent for preventing, treating, or ameliorating a disease caused by a decrease in autophagy function.

For example, Alzheimer's disease, which is a neurodegenerative disease, is triggered by amyloid β produced by cleavage of amyloid-β precursor protein (APP) by secretase. Amyloid β itself is neurotoxic and is deposited on the surface of nerve cells to form plaques. Amyloid β plaques abnormally phosphorylate tau protein, which is a microtubule-binding protein, to form insoluble aggregates in cells. It is considered that such tau protein aggregates accumulate in cells and cause cell death, thereby decreasing acetylcholine and developing Alzheimer's disease. Parkinson's disease is divided into hereditary and sporadic forms. Sporadic Parkinson's disease is a neurodegenerative disease characterized by degeneration of midbrain dopamine neurons, and the cause of which is considered to be a lack of dopamine neurons due to aggregation and accumulation of α-synuclein in nerve cells. It is considered that hereditary Parkinson's disease is caused by accumulation of abnormal mitochondria and denatured proteins that have not been able to be removed due to mutation of Parkin, i.e., a ubiquitin ligase. Such aggregation and accumulation of abnormal proteins and denatured proteins in the cranial nerve tissue are caused by a decrease in autophagy function (Non Patent Literatures 4 and 5).

Therefore, S1PC or a salt thereof is considered to be useful as an agent for preventing, treating, or ameliorating a neurodegenerative disease such as Alzheimer's disease or Parkinson's disease. In fact, S1PC or a salt thereof has exhibited an effect of suppressing the activation of caspase-3 (i.e., a protease related to early apoptosis) in human neuroblasts. Further, it has been confirmed that treatment of S1PC in neuroblasts containing an autophagy inhibitor has suppressed the accumulation of tau protein, that is, had a tau protein-removing effect.

Examples of other diseases that may develop due to decreased autophagy function include Huntington's disease, amyotrophic lateral sclerosis (ALS), muscular dystrophy, Niemann-Pick disease, heart failure, dilated cardiomyopathy, infectious disease, autoimmune disease, obesity, diabetes, arteriosclerosis, and steatohepatitis (Non Patent Literatures 6 to 13).

The autophagy activating agent of the present invention may be a medicine or food which promotes an autophagy function or may be a material or formulation which is added to them.

Further, the food includes a food, a functional food, a food with functional indications, a food for patients, and a food for specified health use, of which concept is to promote the degradation of abnormal proteins and the like and on which the description of the effect based on the function is labeled, if necessary.

The dosage form of a medicine containing S1PC or a salt thereof of the present invention is not particularly limited and a dosage form suitable for oral administration may be used. Preferred is a dosage form suitable for oral administration. Specific examples of the dosage form of formulation for oral administration include solid formulations such as tablets, capsules, fine granules, pills, and pellets; and liquid formulations such as emulsions, solutions, suspensions, and syrups. Such pharmaceutical formulation can be prepared by adding an excipient, a binder, a disintegrant, a lubricant, a colorant, a corrigent, a pH-modifier, for example, if necessary, to S1PC or a salt thereof of the present invention, in accordance with an ordinary method.

The form of a food containing S1PC or a salt thereof of the present invention is not particularly limited. For example, the food may be in various forms such as solid foods, semi-liquid foods, gelled foods, tablets, caplets, and capsules, and specifically may be in form of various foods such as sweets, drinks, seasoning agents, processed sea foods, processed meat foods, bread, and health foods.

Such foods can be produced by appropriately blending food materials used to usually produce these foods with S1PC or a salt thereof of the present invention in accordance with an ordinary method.

The above medicine or food may further contain other substances involved in an effect of promoting the elongation of nerve cell axon and neurotransmission, for example, sulfur-containing amino acids such as γ-glutamyl-S-allyl-cysteine and SAC, herbal medicines such as *Ginseng* and *Ginkgo biloba*, and amino acids such as glutamic acid and GABA. Furthermore, the medicine or food may contain vitamins, lipids, and minerals that relieve inflammation, for example, vitamin C, vitamin E, vitamin B2, vitamin B6, niacin, hesperidin, α-lipoic acid, glutathione, coenzyme Q10, zinc, magnesium, omega-3 fatty acid, and the like.

The preferable daily intake of the above medicine or food varies depending on factors such as a subject who ingests, intake form, types of materials and additives to be simultaneously taken, and the intake interval. Usually, the daily intake in terms of S1PC or a salt thereof is preferably from 0.1 to 2.7 mg/kg and more preferably from 0.3 to 0.9 mg/kg per day. If desired, this daily intake may be divided into two to four times.

Examples of a subject who is administered or ingests include humans who have or are likely to have decreased autophagy functions, humans who are affected with a disease caused by a decrease in autophagy function, such as neurodegenerative disease, cardiovascular disease, lung disease, or infectious disease, and humans who want to prevent the disease.

EXAMPLES

Production Example 1 Production of Plant Extracted Fraction Containing S1PC (1) Ethanol-Extracted Fraction of Garlic About 1 kg of peeled garlic bulbs and about 1000 mL of 30% ethanol were placed in a container and the container was sealed. This container was allowed to stand at room temperature for 1 to 10 months, followed by appropriately stirring. This mixture was separated into a solid and a liquid and the liquid was dried by spray drying to give a yellowish brown powder.

(2) Ethanol-Extracted Fraction of Onion

A peeled onion was cut into two to four pieces. About 5 kg of the cut onions and about 5000 mL of 34% ethanol were placed in a container and the container was sealed. This container was allowed to stand at room temperature for 1 to 10 months, followed by appropriately stirring. This mixture was separated into a solid and a liquid and the liquid was concentrated in vacuo.

(3) Ethanol-Extracted Fraction of Chinese Chive

Washed Chinese chive were cut into a length of about 5 to 10 cm. About 5 kg of the cut leeks and about 5000 mL of 34% ethanol were placed in a container and the container was sealed. This container was allowed to stand at room temperature for 1 to 10 months, followed by appropriately stirring. This mixture was separated into a solid and a liquid and the liquid was concentrated in vacuo.

Production Example 2 Isolation of S1PC from Ethanol-Extracted Fraction of Garlic (1) The ethanol-extracted fraction of garlic obtained in Production Example 1 (1) was put into a dialysis tube having a pore size of 3500 and dialyzed with purified water. The external dialysis solution was passed through a cation exchange resin (Dowex 50W×8 (H+)) and the resin was washed well with purified water. Amino acids adsorbed to the resin was eluted with 2N ammonia and concentrated in vacuo. The concentrate was placed in a silica gel column, followed by column chromatography using a mixture of chloroform/methanol/water as a solvent. Fractions containing a target substance (S1PC) were collected and concentrated. The concentrate was dissolved in water and chromatographed on a reverse phase column for fractionation (octadecyl silyl column) with a solvent (0.1% formic acid). A target substance was collected and the solvent was removed by freeze-drying. The resulting freeze-dried substance was compared in spectrum with the standard substance to be shown below using an NMR (solvent: deuterium oxide) and a mass spectrometer, and the confirmed to be a mixture of trans-S1PC and cis-S1PC (trans-isomer:cis-isomer=8:2).

Trans-S1PC $^{1}$H-NMR (500 MHZ, in $D_2$O-NaOD, δ): 1.76 (d, 3H, J=7.0 Hz), 2.98 (dd, 1H, J=7.5, 14.5 Hz), 3.14 (dd, 1H, J=4.5, 14.5 Hz) 3.69 (dd, 1H, J=4.5, 7.5 Hz), 5.10-5.14 (m, 1H), 6.02 (d, 1H, J=15.5 Hz);

$^{13}$C-NMR (125 MHz, in D-O-NaOD, δ): 17.61, 33.53, 53.70, 119.92, 132.12, 172.73,

HRMS: observed $[M+H]^+$=162.0583, calculated $[M+H]^+$=162.0581

Cis-S1PC $^{1}$H-NMR (500 MHz, in $D_2$O, δ): 1.74 (d, 3H, J=7.0 Hz), 3.21 (dd, 1H, J=7.5, 15.0 Hz), 3.31 (dd, 1H, J=4.5, 15.0 Hz), 3.95 (dd, 1H, J=4.5, 7.5 Hz), 5.82-5.86 (m, 1H), 6.01 (d, 1H, J=9.5 Hz);

$^{13}$C-NMR (125 MHz, in $D_2$O-NaOD, δ): 13.89, 33.88, 54.16, 122.58, 127.78, 172.63.

HRMS: observed $[M+H]^+$=162.0580, calculated $[M+H]^+$=162.0581

(2) Measurement of S1PC in Ethanol-Extracted Fraction of Garlic 500 mg to 1 g of the ethanol-extracted fraction of garlic obtained in Production Example 1 (1) was transferred into a container, a 20 mM hydrochloric acid solution of S-n-3-butenylcysteine as an internal standard was added thereto and the resultant was brought up to 20 mL with 20 mM hydrochloric acid. After well stirring the resulting mixture, a portion thereof was taken out and centrifuged at 1750 G for about 10 minutes. A portion of the obtained supernatant was taken out and subjected to centrifugal filtration (at 15000 rpm for 10 minutes) using a centrifugal filtration unit (Amicon Ultra, cutoff: 3000). 20 µL of the filtrate was taken out and derivatized with an AccQ-Tag Derivatization Kit (Waters). Separately, a reference compound was dissolved in 20 mM hydrochloric acid and subjected to the same operation as the sample to prepare a standard solution for calibration curve. The sample solution and the standard solution were subjected to chromatography with an Acquity UPLC system (Waters) and the content was determined. As a result, S1PC was a dry product (3.7±0.3 mg/g).

Test Example

Autophagy Activation and Effect of Promoting Degradation of Mutant Proteins (1) Preparation of Sample The test solution for evaluating the biological activity was prepared as follows. When evaluating the biological activity, all test solutions were prepared before using.

About 4 mg of S1PC produced in Production Example 1 (a cis- and trans-mixture) was precisely weighed and dissolved in 1 mL of a culture solution. This solution was used as an undiluted solution. The solution was diluted appropriately and used for the test.

(2) Preparation of Human Neuroblasts for Evaluation Test

Human neuroblastoma cell line SH-SY5Y cells were cultured in a Dulbecco's modified Eagle medium supplemented with 10% fetal bovine serum, and antibiotic penicillin-streptomycin solution, and the cultured cells were used as cells for evaluation test.

(3) Western Blotting (a) Autophagy Activation and Tau Protein-Removing Effect

Okadaic acid (at a concentration of 100 nM) and S1PC (at concentrations of 0.03, 0.1, and 0.3 mM) were added to the human neuroblasts for evaluation test prepared in (2) above, and the cells were cultured for 6 hours. After culturing, the cultured cells were washed with a phosphate buffer, and then lysed with RIPA cell lysis buffer (manufactured by Millipore Corporation) diluted 10-fold with purified water containing a protease/phosphatase cocktail inhibitor (manufactured by Thermo Fisher Scientific K.K.). After that, centrifugation was conducted (at 10000 rpm, for 10 minutes, at 4° C.), and the supernatant was used as a cell extract. This cell extract was used to conduct analysis by western blotting in accordance with a usual method. An anti-Atg7 antibody (manufactured by Cell Signaling Technology, Inc.), an anti-4T-tau antibody (manufactured by Wako Pure Chemical Industries, Ltd.), and an anti-β-actin antibody (manufactured by Wako Pure Chemical Industries, Ltd.) were used as antibodies. The results are shown in FIG. 1. S1PC increased Atg7 expression and promoted removal of tau proteins.

Figure 2:
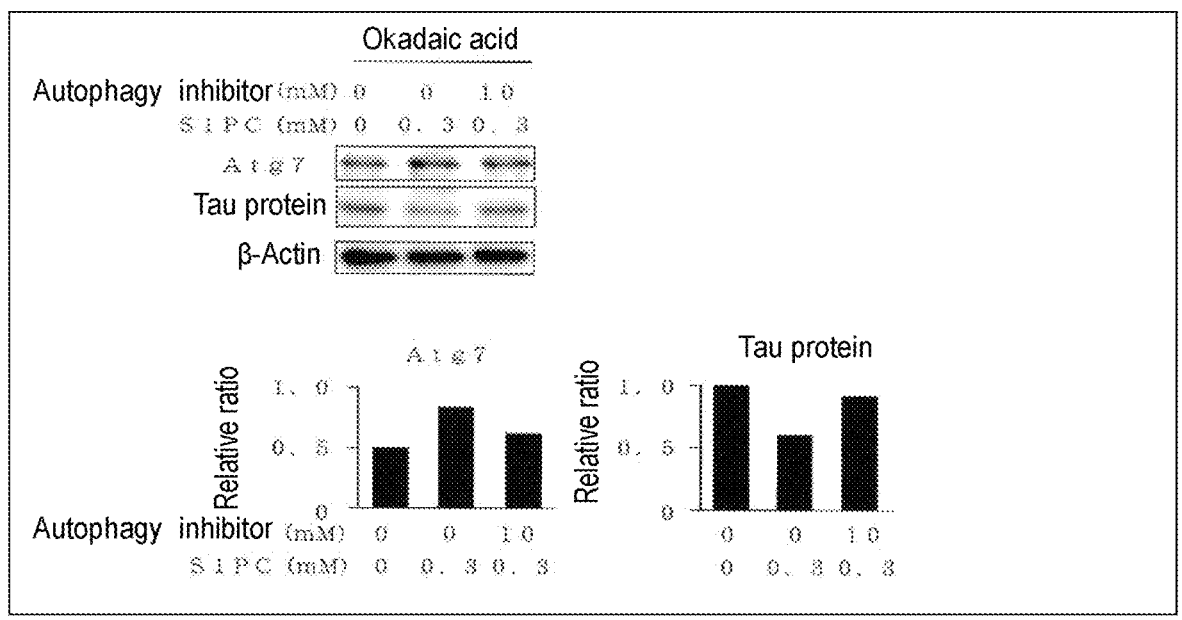
FIG. 2 illustrates an influence of an autophagy inhibitor on the autophagy activating effect and the tau protein-removing effect of S1PC.

(b) Tau Protein-Removing Effect Via Autophagy 10 nM okadaic acid, 0.3 mM S1PC, and 10 mM autophagy inhibitor (3-methyladenine) were added to the human neuroblasts for evaluation test prepared in (2) above, and the cells were cultured for 24 hours. A cell extract was prepared in the same manner as in (a) above, and analyzed by western blotting in accordance with a usual method. An anti-Atg7 antibody (manufactured by Cell Signaling Technology, Inc.), an anti-4T-tau antibody (manufactured by Wako Pure Chemical Industries, Ltd.), and an anti-β-actin antibody (manufactured by Wako Pure Chemical Industries, Ltd.) were used as antibodies. The results are shown in FIG. 2.

The Atg7 expression-increasing effect and the tau protein-removing effect of S1PC were suppressed by adding the autophagy inhibitor. From the above results, it can be said that S1PC exerted the tau protein-removing effect via the autophagy activating effect.

(c) Apoptosis Inhibitory Effect 100 nM okadaic acid and 0.3 mM S1PC were added to the human neuroblasts for evaluation test prepared in (2) above, and the cells were cultured for 6 hours. A cell extract was prepared in the same manner as in (a) above, and analyzed by western blotting in accordance with a usual method. An anti-caspase-3 antibody (manufactured by Cell Signaling Technology, Inc.) and an anti-β-actin antibody (manufactured by Wako Pure Chemical Industries, Ltd.) were used as antibodies. The results are shown in FIG. 3.

Figure 3:
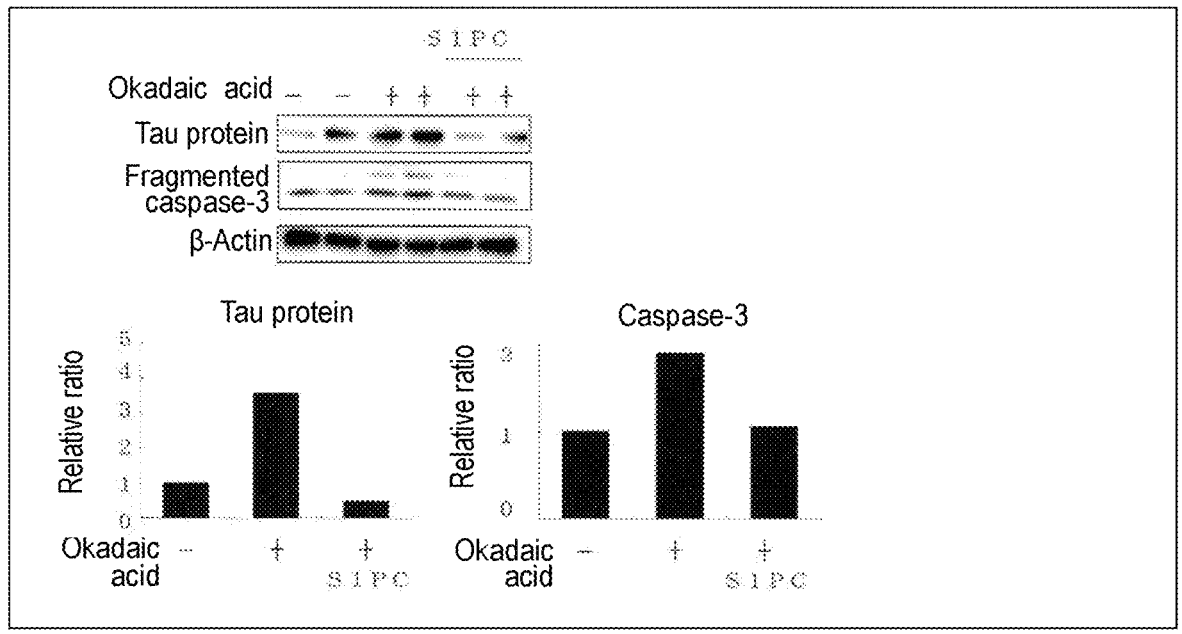
FIG. 3 illustrates an apoptosis inhibitory effect of S1PC.

From FIG. 3, it was confirmed that S1PC suppressed the activation of caspase-3.

Since caspase-3 induces apoptosis by cleaving the target protein, it can be said that S1PC has an effect of suppressing apoptosis.

(d) Comparison of Tau Protein-Removing Effect with SAC 50 nM okadaic acid and 0.3 mM S1PC or SAC were added to the human neuroblasts for evaluation test prepared in (2) above, and the cells were cultured for 6 hours. A cell extract was prepared in the same manner as in (a) above, and analyzed by western blotting in accordance with a usual method. An anti-4T-tau antibody (manufactured by Wako Pure Chemical Industries, Ltd.) and an anti-β-actin antibody (manufactured by Wako Pure Chemical Industries, Ltd.) were used as antibodies. The results are shown in FIG. 4.

Figure 4:
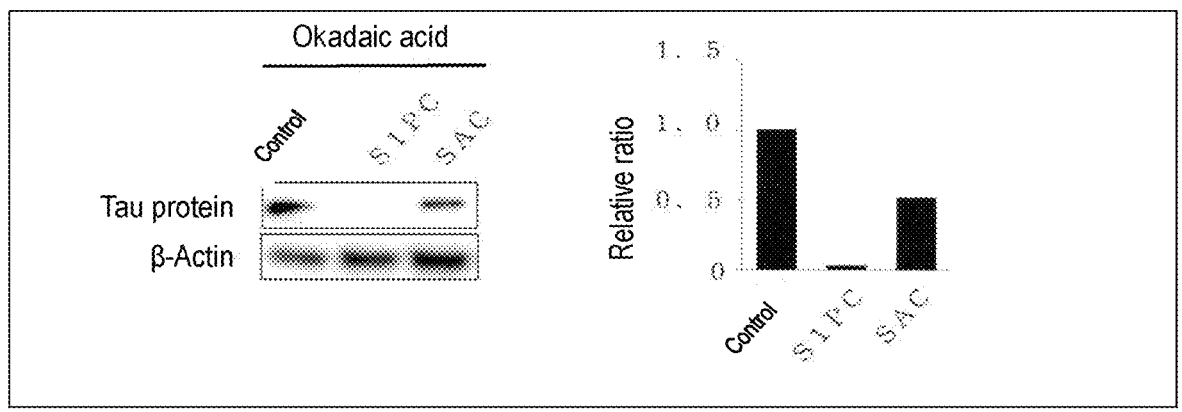
FIG. 4 illustrates tau protein-removing effects of S1PC and SAC.

From FIG. 4, the tau protein was decreased by adding S1PC, and its effect was superior to SAC. Therefore, S1PC is considered to be useful for neurodegenerative diseases such as Alzheimer's disease accompanied by tau protein accumulation.

(e) α-Synuclein Protein-Removing Effect Via Autophagy

Figure 5:
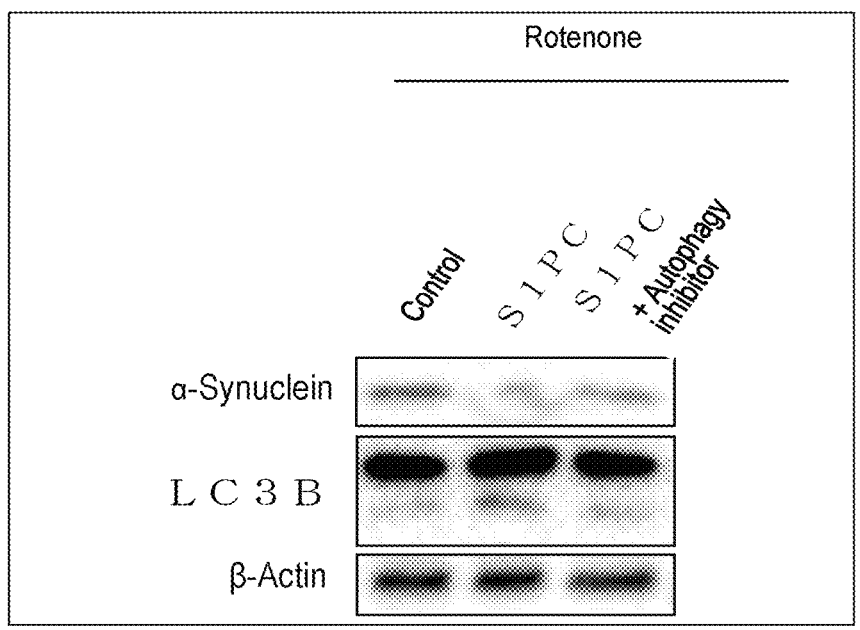
FIG. 5 illustrates an α-synuclein protein-removing effect of S1PC.

10 µM rotenone, 0.3 mM S1PC, and 1 mM autophagy inhibitor (3-methyladenine) were added to the human neuroblasts for evaluation test prepared in (2) above, and the cells were cultured for 3 hours. A cell extract was prepared in the same manner as in (a) above, and analyzed by western blotting in accordance with a usual method. An anti-α-synuclein antibody, an anti-LC3B antibody (manufactured by Cell Signaling Technology, Inc.), and an anti-β-actin antibody (manufactured by MEDICAL & BIOLOGICAL LABORATORIES CO., LTD.) were used as antibodies. The results are shown in FIG. 5.

The LC3B-II expression-increasing effect and the α-synuclein protein-removing effect of S1PC were suppressed by adding the autophagy inhibitor.

From the above results, it can be said that S1PC exerted the α-synuclein protein-removing effect via the autophagy activating effect.

Figure 6:
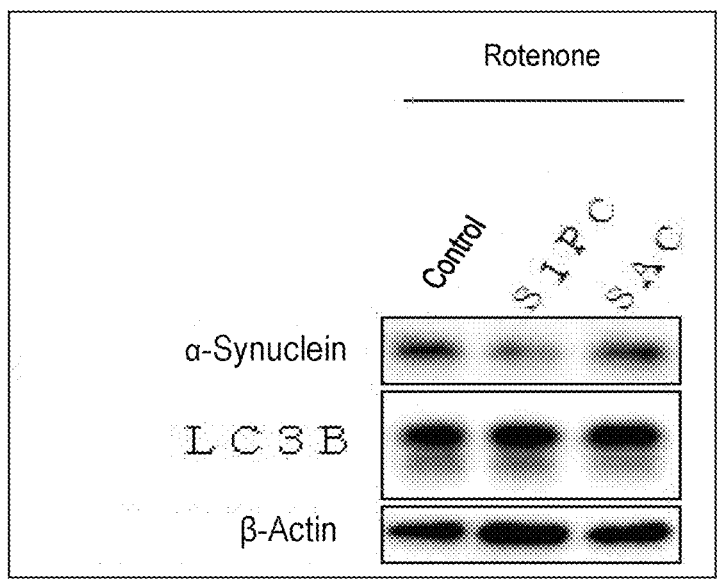
FIG. 6 illustrates an α-synuclein protein-removing effect of S1PC (as compared with SAC).

(f) Comparison of α-Synuclein Protein-Removing Effect with SAC 500 nM rotenone, and 0.3 mM S1PC or SAC were added to the human neuroblasts for evaluation test prepared in (2), and the cells were cultured for 3 hours. A cell extract was prepared in the same manner as in (a) above, and analyzed by western blotting in accordance with a usual method. An anti-α-synuclein antibody, an anti-LC3B antibody (manufactured by Cell Signaling Technology, Inc.), and an anti-β-actin antibody (manufactured by MEDICAL & BIOLOGICAL LABORATORIES CO., LTD.) were used. The results are shown in FIG. 6. The α-synuclein protein was decreased by adding S1PC, and its effect was superior to SAC. Therefore, S1PC is considered to be useful for Parkinson's disease, for example, accompanied by α-synuclein protein accumulation.

The invention claimed is:

1. A method for treating or ameliorating a neurodegenerative disease comprising administering isolated S-1-propenylcysteine or a salt thereof to a subject.

2. The method of claim 1, wherein the neurodegenerative disease is treated, or ameliorated via autophagy activation.

3. The method of claim 1, wherein the amount of a trans-isomer and a cis-isomer of the S-1-propenylcysteine or a salt thereof is 100%, the proportion of the trans-isomer in the S-1-propenylcysteine is from 50 to 100%.

4. The method of claim 1, wherein the S-1-propenylcysteine or a salt thereof is derived from at least one *Allium* plant selected from the group consisting of garlic, onion, elephant garlic, Chinese chive, and spring onion.

5. The method of claim 4, wherein the S-1-propenylcysteine or a salt thereof is obtained by extracting the *Allium* plant in a 10 to 50% ethanol solution at 0 to 80° C. for 1 month or more, allowing the obtained extract to adsorb to a cation exchange resin, eluting the adsorbate with 0.1 to 3 N ammonia water, subjecting the eluate to silica gel column chromatography and/or reverse phase column chromatography, and collecting the resulting eluate.

6. The method of claim 1 wherein the neurodegenerative disease is selected from the group consisting of Alzheimer's disease, Parkinson's disease, Huntington's disease, and amyotrophic lateral sclerosis.

7. The method of claim 1 wherein the neurodegenerative disease is selected from the group consisting of Alzheimer's disease and Parkinson's disease.

8. The method of claim 1, wherein the neurodegenerative disease comprises Alzheimer's disease.

9. The method of claim 1, wherein the S-1-propenylcysteine or a salt thereof is administered orally in a formulation comprising at least one of an excipient, a binder, a disintegrant, a lubricant, a colorant, a corrigent, and a pH-modifier.

10. The method of claim 9, wherein the formulation is in the form of a tablet, capsule, fine granule, pill, pellet, emulsion, solution, suspensions, or syrup.

11. The method of claim 1, wherein the S-1-propenylcysteine or a salt thereof is added to a food.

12. The method of claim 11, wherein the food is at least one of a gelled, solid food, semi-liquid food, sweet, drink, seasoning agent, processed meat and seafood, bread, and health food.

13. A method for treating or ameliorating a neurodegenerative disease comprising administering a composition consisting essentially of S-1-propenylcysteine or a salt thereof to a subject.

14. The method of claim 13, wherein the neurodegenerative disease is treated, or ameliorated via autophagy activation.

15. A method for treating or ameliorating a neurodegenerative disease comprising administering S-1-propenylcysteine or a salt thereof to a subject,
   wherein a garlic extract obtained by extracting garlic in an ethanol aqueous solution for at least one month is not administered to the subject.

16. The method of claim 15, wherein the neurodegenerative disease is treated, or ameliorated via autophagy activation.

\* \* \* \* \*